US011179468B2

(12) United States Patent
Teja et al.

(10) Patent No.: US 11,179,468 B2
(45) Date of Patent: Nov. 23, 2021

(54) FULVESTRANT FORMULATIONS

(71) Applicant: Eagle Pharmaceuticals, Inc., Woodcliff Lake, NJ (US)

(72) Inventors: Bulusu Bhanu Teja, Hyderabad (IN); Nagesh R. Palepu, Southampton, PA (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

(21) Appl. No.: 13/858,771

(22) Filed: Apr. 8, 2013

(65) Prior Publication Data
US 2013/0267489 A1 Oct. 10, 2013

Related U.S. Application Data

(60) Provisional application No. 61/621,785, filed on Apr. 9, 2012.

(51) Int. Cl.
*A61K 47/22* (2006.01)
*A61K 47/20* (2006.01)
(Continued)

(52) U.S. Cl.
CPC ............ *A61K 47/22* (2013.01); *A61K 9/0019* (2013.01); *A61K 31/565* (2013.01); *A61K 47/10* (2013.01); *A61K 47/14* (2013.01); *A61K 47/20* (2013.01)

(58) Field of Classification Search
CPC .... A61K 31/565; A61K 31/575; A61K 31/56; A61K 47/22; A61K 47/10; A61K 9/0019;
(Continued)

(56) References Cited

U.S. PATENT DOCUMENTS 4,659,516 A   4/1987 Bowler et al.
4,719,239 A * 1/1988 Muller ................. A61K 9/0014
                                              514/785
(Continued)

FOREIGN PATENT DOCUMENTS

GB         2087721 A    6/1982
KR    1020100018741 A    2/2010
(Continued)

OTHER PUBLICATIONS

"Scientific Discussion", EMEA. Nov. 21, 2006, pp. 1-33 (Retrieved from Internet: URL: http://web.archive.org/web/20061121015215// http://www.emea.europa.eu/humandocs/PDFs/EPAR/faslodex/ 610303en6.pdf).
(Continued)

*Primary Examiner* — Savitha M Rao
*Assistant Examiner* — Andrew P Lee
(74) *Attorney, Agent, or Firm* — BakerHostetler

(57) ABSTRACT

Long term storage stable fulvestrant-containing compositions are disclosed. The compositions can include fulvestrant; a solvent selected from dimethyl sulfoxide (DMSO), glycofurol, N-methyl pyrrolidone, and mixtures thereof; an oil mixture selected from a mixture of caprylic and capric triglycerides, a mixture of caprylic, capric and linoleic triglycerides, a mixture of caprylic, capric and succinic triglycerides, and a mixture of propylene glycol dicaprylate and propylene glycol dicaprate; and a sustained release member selected from benzyl benzoate, dihydrolipoic acid, benzyl alcohol and lipoic acid. The fulvestrant-containing compositions have less than about 5% total impurities, on a normalized peak area response ("PAR") basis as determined by high performance liquid chromatography ("HPLC") at a wavelength of 223 nm, after at least about 24 months of storage at a temperature of from about 5° C. to about 25° C.

17 Claims, 2 Drawing Sheets

(51) Int. Cl.
*A61K 47/14* (2017.01)
*A61K 31/565* (2006.01)
*A61K 47/10* (2017.01)
*A61K 9/00* (2006.01)

(58) Field of Classification Search
CPC .. A61K 47/20; A61K 47/14; C07J 9/00; C07J 1/00
See application file for complete search history.

(56) References Cited

U.S. PATENT DOCUMENTS

| | | | |
|---|---|---|---|
| 5,462,726 | A | 10/1995 | Lodge |
| 6,531,139 | B1 | 3/2003 | Gao et al. |
| 6,774,122 | B2 | 8/2004 | Evans et al. |
| 7,115,565 | B2 | 10/2006 | Gao et al. |
| 2002/0049158 | A1 | 4/2002 | Woo et al. |
| 2002/0102280 | A1 | 8/2002 | Anderson |
| 2004/0047835 | A1 | 3/2004 | Bianco |
| 2004/0175402 | A1 | 9/2004 | Gellert et al. |
| 2005/0043285 | A1 | 2/2005 | Evans et al. |
| 2006/0003002 | A1 | 1/2006 | Fikstad et al. |
| 2006/0172014 | A1 | 8/2006 | Curd et al. |
| 2006/0189679 | A1 | 8/2006 | Holton et al. |
| 2006/0264357 | A1 | 11/2006 | Zikria et al. |
| 2007/0116729 | A1 | 5/2007 | Palepu |
| 2007/0237740 | A1 | 10/2007 | Reddington et al. |
| 2007/0269379 | A1 | 11/2007 | Mitragotri et al. |
| 2007/0281934 | A1 | 12/2007 | Buggy et al. |
| 2008/0146651 | A1 | 6/2008 | Jee et al. |
| 2008/0319048 | A1 | 12/2008 | Palepu et al. |
| 2009/0181068 | A1* | 7/2009 | Dunn ............................ 424/426 |
| 2009/0227549 | A1* | 9/2009 | Palepu .......................... 514/171 |
| 2009/0318543 | A1 | 12/2009 | Vu et al. |
| 2010/0015195 | A1 | 1/2010 | Jain et al. |

FOREIGN PATENT DOCUMENTS

| | | |
|---|---|---|
| WO | 97/21440 A1 | 6/1997 |
| WO | 01/51056 A1 | 7/2001 |
| WO | 02092077 A2 | 11/2002 |
| WO | 2005039554 A2 | 5/2005 |
| WO | 2005097105 A1 | 10/2005 |
| WO | 2007020085 A2 | 2/2007 |
| WO | 2007033434 A1 | 3/2007 |
| WO | 2009090614 A2 | 7/2009 |
| WO | 2009111057 A2 | 9/2009 |

OTHER PUBLICATIONS

Bross et al., "Fulvestrant in Postmenopausal Women with Advanced Breast Cancer", Clinical Cancer Research. Oct. 1, 2003, vol. 9 pp. 4309-4317.
Castor Oil MSDS Material Safety Data Sheet, Science Lab.com Chemicals & Laboratory Equipment. Mar. 23, 2006, pp. 1 (Retrieved from Internet: URL: http://web.archive.org/web/20060323231047/http:/www.sciencelab.com/xMSDS-Castor_oil-9927126.
International Search Report and Written Opinion of the International Search Authority in PCT/US09/01437.
Supplementary European Search Report based on Application No. EP 09716692, dated Sep. 18, 2013. (2 pages).
Weller, "GLYCOFUROL", Handbook of Pharmaceutical Excipients, 5th ed., 2006, pp. 313-314.
Chinese Office Action based on Chinese Application No. 200980108157.3 dated Nov. 7, 2011. (9 pages).
Du Wenting, et al. "Research progression of water-soluble derivatives of paclitaxe", The Chinese Journal of Modern Applied Pharmacy, vol. 22, No. 1, pp. 29-31.
Japanese Office Action based on Japanese Application No. 2010-549670 dated Aug. 6, 2013 (5 pages). (Enlgish Translation).
Written Opinion of the International Searching Authority based on International Application No. PCT/IN2013/000235, dated Oct. 14, 2014 (7 pages).
International Search Report based on International Application No. PCT/IN2013/000235 dated Aug. 12, 2013 (4 pages).

* cited by examiner

FULVESTRANT FORMULATIONS

CROSS-REFERENCE TO RELATED APPLICATION

This patent application claims priority under 35 U.S.C. § 119(e) to U.S. Provisional Patent Application No. 61/621,785, filed Apr. 9, 2012, entitled "FULVESTRANT FORMULATIONS", the contents of which are incorporated by reference herein in its entirety.

BACKGROUND OF THE INVENTION

Fulvestrant injection for intramuscular administration is an estrogen receptor antagonist is marketed as FASLODEX. The chemical name is 7-alpha-[9-(4,4,5,5,5-penta fluoro-pentylsulphinyl)nonyl]estra-1,3,5-(10)-triene-3,17-beta-diol. The molecular formula is $C_{32}H_{47}F_5O_3S$ and its structural formula is:

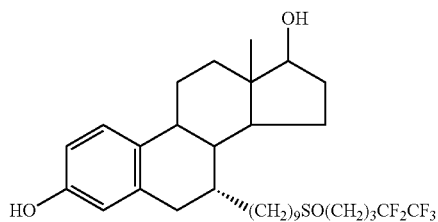

FASLODEX is supplied in sterile single patient pre-filled syringes containing 50-mg/ml fulvestrant either as 5 ml or 2.5 ml injections to deliver the required monthly dose. The current dosing regimen includes injecting 500 mg (10 ml injection). Most of the formulation contains castor oil, which results in an extremely painful injection. Typical side effects of castor oil and its derivatives are (a) skin and other irritation at the administration site; (b) allergic reaction; (c) gastrointestinal disturbances even though the product is not administered to the GI tract. Hence there is a need to find a more concentrated system which is free of castor oil, to allow low volume administration of medicament and reduction in pain.

SUMMARY OF THE INVENTION

In some aspects of the invention, the fulvestrant-containing compositions include a solvent selected from dimethyl sulfoxide (DMSO), glycofurol, N-methyl pyrrolidone, and mixtures thereof; an oil mixture selected from i) caprylic and capric triglycerides, ii) caprylic, capric and linoleic triglycerides, iii) caprylic, capric and succinic triglycerides, and iv) propylene glycol dicaprylate and propylene glycol dicaprate; and a sustained release member selected from benzyl benzoate, dihydrolipoic acid, benzyl alcohol or lipoic acid. The amount of fulvestrant included in the compositions is preferably from about 45 mg/ml to about 250 mg/ml. Still further aspects of the invention include methods of treatment using fulvestrant-containing compositions.

One of the advantages of the inventive compositions is that they have substantially improved long term stability when compared to currently available formulations. For example, the inventive fulvestrant compositions are substantially free of impurities after at least about 24 months at a temperature of from about 5° C. to about 25° C. The inventive formulations are advantageously ready to use and preferably administered intramuscularly, but can be administered by suitable injection routes that are suitable for the fulvestrant active agent.

Another advantage of the inventive compositions is that they are substantially free or completely free of castor oil and castor oil derivatives.

DETAILED DESCRIPTION OF THE INVENTION

Figure 1:
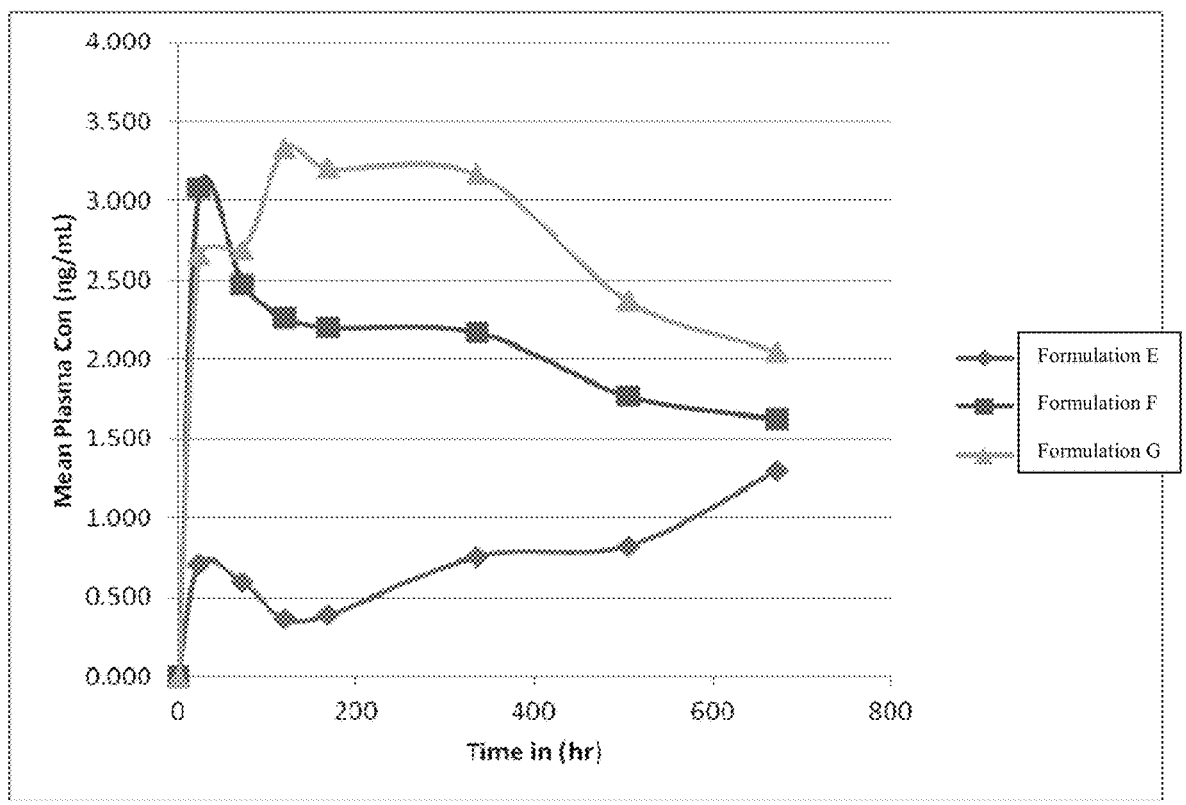
FIG. 1 is data corresponding to Example 2.

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT<1 elutes before the main peak, and any peak with an RRT>1 elutes after the main peak.

For purposes of the present invention, "substantially free of impurities" shall be understood to include fulvestrant-containing compositions in which the amount of total impurities is less than about 5%, as calculated on a normalized peak area response ("PAR") basis as determined by high performance liquid chromatography ("HPLC") at a wavelength of 223 nm, after a period of about 24 months at a temperature of from about 5° C. to about 25° C. The amount of impurities is further calculated as being based upon the original amount fulvestrant (or salt thereof) being present in the composition or formulation.

As used herein, "substantially free", when referencing the amount of castor oil and castor oil derivatives in the fulvestrant-containing formulations described herein means not more than about 5%, preferably not more than about 4%, about 3%, about 2%, about 1%, about 0.5%, about 0.1%, and about 0.01% (100 ppm). More preferably, the fulvestrant-containing compositions include undetectable amounts of castor oil and castor oil derivatives with the use of standard analytic equipment, i.e. zero. Each of the % amounts being with reference to the complete formulation.

In accordance with one aspect of the invention, there are provided long term storage stable fulvestrant-containing compositions including:
  a) fulvestrant;
  b) a solvent selected from dimethyl sulfoxide (DMSO), glycofurol, N-methyl pyrrolidone, and mixtures thereof;
  c) an oil mixture selected from:
    i) a mixture of caprylic and capric triglycerides,
    ii) a mixture of caprylic, capric and linoleic triglycerides,
    iii) a mixture of caprylic, capric and succinic triglycerides, and
    iv) a mixture of propylene glycol dicaprylate and propylene glycol dicaprate; and
  d) a sustained release member selected from benzyl benzoate, dihydrolipoic acid, benzyl alcohol and lipoic acid.

The total impurities in the inventive compositions resulting from the degradation of the fulvestrant in the compositions is less than about 5% PAR as determined by HPLC at a wavelength of 223 nm, after at least about 24 months of storage at a temperature of from about 5° C. to about 25° C., and thus have long term stability for at least the same period of time or longer. Preferably, the fulvestrant-containing compositions demonstrate long term storage stability for at least about 36 months when stored under the conditions described herein. In one embodiment, the amount of total impurities in the inventive compositions resulting from the degradation of the fulvestrant is less than about 3% PAR as determined by HPLC at a wavelength of 223 nm after at least about 24 months at a temperature of from about 5° C. to about 25° C. Preferably, the amount of any individual degradant in the inventive compositions does not exceed 2% PAR as determined by HPLC at a wavelength of 223 nm after storage periods of at least about 24 months at a temperature of from about 5° C. to about 25° C.

In some aspects of the invention, the solvent is present in an amount of from about 20% (v/v) to about 40% (v/v). Preferably, the solvent is present in an amount of about 33% (v/v). In some aspects of the invention, the oil mixture is present in an amount of from about 20% (v/v) to about 50% (v/v). Preferably, the oil mixture is present in an amount of about 25% (v/v). In other embodiments, the sustained release member is present in an amount of from about 20% (v/v) to about 50% (v/v). Preferably, the sustained release member is present in an amount of about 42% (v/v). Within this aspect, the volume ratio of solvent:oil mixture:sustained release member is about 1 to about 2.5:about 0.9 to about 2.5:about 0.9 to about 2.5. Preferably, the volume ratio of solvent:oil mixture:sustained release member is about 1.3: about 1:about 1.7.

In some embodiments, the solvent is DMSO, glycofurol or N-methyl pyrrolidone. In other embodiments of the invention, however, the solvent is a mixture of DMSO and glycofurol. Within this aspect, the volume ratio of DMSO: glycofurol:oil mixture:sustained release member is about 0.9 to about 1.1:about 0.9 to about 1.1:about 0.9 to about 1.1:about 0.9 to about 1.1. Preferably, the volume ratio of DMSO:glycofurol:oil mixture:sustained release member is about 1:about 1:about 1:about 1.

In some aspects of the invention, the oil mixture is selected from: i) a mixture of caprylic and capric triglycerides; ii) a mixture of caprylic, capric and linoleic triglycerides; iii) a mixture of caprylic, capric and succinic triglycerides; and iv) a mixture of propylene glycol dicaprylate and propylene glycol dicaprate. The oil mixture in the fulvestrant-containing compositions according to several aspects of the invention can be mixtures of the fatty acid triglycerides such as the products marketed under the name MIGLYOL, i.e. MIGLYOL 810, 812, 818, 829 and 840. The product information sheet for MIGLYOL is incorporated by reference herein in its entirety. Preferably, the oil mixture is caprylic and capric triglycerides, such as MIGLYOL 812, preferably including 50-64% $C_8$ and 30-45% $C_{10}$ fatty acids.

Without meaning to be bound by any theory or hypothesis, the member can have the effect of allowing for steady state concentrations to be reached, i.e. sustaining the release of fulvestrant and maintaining the duration of circulation in the blood stream for extended periods, such as at least about 15 days, and preferably at least about 28 days. In some aspects of the invention, the member is selected from pharmaceutically acceptable compounds known to increase the duration of circulation of a drug in the blood stream, such as benzyl benzoate, dihydrolipoic acid, benzyl alcohol and lipoic acid. The member in the fulvestrant-containing compositions according to several aspects of the invention is benzyl benzoate. In some aspects of the invention, the inventive compositions achieve steady-state concentrations of fulvestrant in vivo after the first to sixth dose, in other aspects steady state concentrations of fulvestrant are achieved after the fourth to sixth dose. Without meaning to be bound by any theory or hypothesis, attainment of steady state concentration in vivo for fulvestrant shall be understood to be a level sufficient to therapeutically control estrogen levels in the patient.

In some aspects of the invention, the fulvestrant concentration in the inventive compositions is from about 45 mg/ml to about 250 mg/ml, preferably from about 50 mg/ml to about 150 mg/ml. Preferably, the fulvestrant concentration is from about 100 mg/ml to about 125 mg/ml. It will be understood that compositions containing any useful concentration within the ranges, i.e. 45, 50, 55, 60, 70, 75, 80, 90, 100, 125, 150 . . . 250 are contemplated. In other embodiments, the fulvestrant concentration in the composition is about 50 mg/ml. In other embodiments, the fulvestrant concentration is about 100 mg/ml. In alternative aspects, the fulvestrant is outside these ranges, but the amounts will be sufficient for single or multiple administrations of dosages generally regarded as effective amounts. In some aspects of the invention, pharmaceutically acceptable salts of fulvestrant are also contemplated.

The fulvestrant-containing compositions according to the invention may include at least one antioxidant that is pharmaceutically acceptable for use in human and veterinary formulations. The antioxidant is not limited to those currently regarded as safe by any regulatory authority. For example, the antioxidant can be selected from among lipoic acid, dihydrolipoic acid, methionine, sulpha-containing amino acids, acetone sodium bisulfate, propyl gallate, butylated hydroxytoluene ("BHT"), butylated hydroxyanisole ("BHA") and sodium formaldehyde sulfoxylate. Suitable antioxidant concentrations in the compositions can range from about 2.5 mg/mL to about 35 mg/mL, and preferably from about 5 mg/mL to about 20 mg/mL or from about 10 mg/mL to about 15 mg/mL. In some other embodiments, the concentration of the antioxidant in the fulvestrant-containing compositions is about 5 mg/mL.

Other additives which may be included in the compositions include polyethylene glycol (PEG), propylene glycol (PG), phospholipids, and poloxamers, including those products marketed under the name LUTROL. The molecular weight of the PEG will be within the range of pharmaceutically acceptable weights, although PEG 400 is preferred in many aspects of the invention.

In view of the foregoing, some preferred long term storage stable fulvestrant-containing compositions in accordance with the invention include:

I. a) fulvestrant;
   b) DMSO;
   c) a mixture of caprylic and capric triglycerides, i.e. MIGLYOL 812; and
   d) benzyl benzoate;
   wherein the DMSO is present in an amount of about 33% (v/v), the mixture of caprylic and capric triglycerides is present in an amount of about 25% (v/v), and the benzyl benzoate is present in an amount of about 42% (v/v); or II. a) fulvestrant;
    b) DMSO;
    c) a mixture of caprylic and capric triglycerides;
    d) benzyl benzoate; and
    e) glycofurol;

wherein the volume ratio of DMSO:mixture of caprylic and capric triglycerides:benzyl benzoate:glycofurol is about 1:about 1:about 1:about 1.

Each of these compositions have the same stability described above, i.e. less than about 5% total impurities PAR as determined by HPLC at a wavelength of 223 nm, after at least about 24 months of storage at a temperature of from about 5° C. to about 25° C. Preferably, the compositions are stable for at least about 36 months of storage at a temperature of from about 5° C. to about 25° C.

Another embodiment of the invention provides methods of treating a fulvestrant treatable condition in mammals. The methods include administering to a patient in need thereof an effective amount of one of the fulvestrant-containing compositions described herein. Since the active ingredient portion of the inventive composition is an FDA-approved drug, those of ordinary skill will recognize that the doses of fulvestrant employed in this aspect of the invention will be similar to those employed in any treatment regimens designed for fulvestrant as marketed under the trade name FASLODEX. The patient package insert containing dosing information is incorporated herein by reference. The methods of treatment also include administering the inventive formulations for any purpose or physical condition for which fulvestrant has been indicated as being useful. Examples of fulvestrant treatable conditions include benign or malignant disease of the breast or reproductive tract. In some aspects the conditions are hormonal dependent.

In some aspects of the invention, the fulvestrant-containing compositions will be formulated for intramuscular injection, although other injection routes that are compatible with fulvestrant and the excipients are also contemplated as within the invention.

EXAMPLES

The following examples serve to provide further appreciation of the invention but are not meant in any way to restrict the effective scope of the invention.

Example 1

Fulvestrant-containing compositions were prepared as follows:

Formulation A (Inventive) was prepared by dissolving 50 mg fulvestrant in a 1 mL solution including DMSO:glycofurol:MIGLYOL 812, i.e. a mixture of caprylic and capric triglycerides:benzyl benzoate in a volume ratio of 1:1:1:1.

Formulation B (Inventive) was prepared in the same manner as Formulation A, except that the fulvestrant concentration was 100 mg/mL.

Formulation C (Inventive) was prepared by dissolving 125 mg fulvestrant in a 1 mL solution including 33% (v/v) DMSO, 25% (v/v) MIGLYOL 812, and 42% (v/v) benzyl benzoate.

Formulation D (Inventive) was prepared by dissolving 100 mg fulvestrant in a 1 mL solution including 33% (v/v) DMSO, 25% (v/v) MIGLYOL 812, and 42% (v/v) benzyl benzoate.

The samples were maintained at 40° C. and analyzed periodically for drug content and total impurities at intervals indicated in Table 1 below. The results obtained are presented in Table 1.

TABLE 1

Stability of Fulvestrant

| Formulation | Temp. | Time Period | Conc. (mg/mL) | % of Initial | % of Total |
|---|---|---|---|---|---|
| Formulation A - 50 mg/mL DMSO:Glycofurol: Miglyol 812:Benzyl benzoate (1:1:1:1) qs to 1 mL | 40° C. | Initial | 49.2 | 100 | 0.06 |
| | | 30 days | 49.0 | 100.4 | 0.15 |
| | | 70 days | 49.0 | 100 | 0.15 |
| | | 168 days | 48.9 | 100 | 0.18 |
| Formulation B - 100 mg/mL DMSO: Benzyl benzoate: Miglyol 812: Glycofurol (1:1:1:1) qs to 1 mL | 40° C. | Initial | 101.8 | 100 | 0.34 |
| | | 1 month | 101.4 | 99.6 | 0.42 |
| | | 2 months | 100.9 | 99.1 | 0.41 |
| | | 3 months | 100.8 | 99.0 | 0.44 |
| | | 6 months | 100.6 | 98.8 | 0.45 |
| Formulation C - 125 mg DMSO:Benzyl benzoate:Miglyol 812 (0.33:0.42:0.25) qs to 1 mL | 40° C. | Initial | 123.6 | 100 | 0.29 |
| | | 1 month | 123.6 | 100.0 | 0.31 |
| | | 2 months | 122.8 | 99.4 | 0.32 |
| | | 3 months | 121.4 | 98.2 | 0.28 |
| | | 6 months | 121.4 | 98.2 | 0.28 |
| Formulation D - 100 mg DMSO:Benzyl benzoate:Miglyol 812 (0.33:0.42:0.25) qs to 1 mL | 40° C. | Initial | 101.7 | 100 | 0.28 |
| | | 1 month | 100.8 | 99.1 | 0.30 |
| | | 2 months | 100.6 | 98.9 | 0.32 |
| | | 3 months | 100.2 | 98.5 | 0.33 |
| | | 6 months | 100.1 | 98.4 | 0.34 |

Note
In Table 1 the total % impurities include total contributions from peaks at various RRTs.

As shown in Table 1, the inventive fulvestrant formulations are very stable in solutions containing at least one solvent, an oil mixture, and a sustained release member. Table 1 shows that fulvestrant, when dissolved at a concentration of from 50 mg/mL to 125 mg/mL, in DMSO, benzyl benzoate and Miglyol 812, with or without glycofurol, had less than about 0.5% total impurities after at least 1 month, and at least as long as 6 months, storage at 40° C.

The data presented in Table 1 translates to fulvestrant-containing compositions including at least one solvent, an oil mixture and a sustained release member having a shelf life of at least about 24 months at 5° C. or 25° C. In fact, the inventive compositions are expected to be stable for at least 36 months under ambient storage conditions. In contrast, a sample related to FASLODEX requires refrigerated storage, and therefore, is not as stable as the inventive compositions and would not be suitable for long-term storage as described herein.

Example 2

Fulvestrant-containing compositions (Formulation E, Formulation F and Formulation G) were prepared as follows:

Formulation E (Control) was prepared as a control with recinolic acid, which is a major component of castor oil. Formulation E was prepared by dissolving 50 mg fulvestrant in a 1 mL solution including recinolic acid and PG in a molar ratio of 1:1 recinolic acid:PG.

Formulation F (Inventive) was prepared by dissolving 50 mg fulvestrant in a 1 mL solution including N-methyl pyrrolidone:glycofurol:MIGLYOL 812:benzyl benzoate in a volume ratio of 1:1:1:1.

Formulation G (Control) FASLODEX was obtained commercially from AstraZeneca, and includes fulvestrant at a concentration of 50 mg/mL in a solution including 10%

(w/v) ethanol, 10% (w/v) benzyl alcohol, 15% (w/v) benzyl benzoate and castor oil added to 1 mL.

The PK profiles of Formulation E, Formulation F, and Formulation G were evaluated in rabbits.

As shown in FIG. 1, Formulation E showed lowest Cmax and the lowest mean plasma concentration. Inventive Formulation F exhibited a comparable PK profile to Formulation G. The PK profile of Formulation E, which shows the "low" levels, is inferior to that of inventive Formulation F and Formulation G. Accordingly, inventive Formulation F achieves a comparable PK profile to Formulation G, and is long term storage stable for at least 36 months under ambient conditions, without the inclusion of castor oil.

Example 3

Fulvestrant-containing compositions (Formulation A, Formulation H and Formulation G) were prepared as follows:

Formulation A (Inventive) was prepared as described above in Example 1.

Formulation H (Inventive) was prepared by dissolving 50 mg fulvestrant in a 1 mL solution including 33% (v/v) DMSO, 25% (v/v) MIGLYOL 812, and 42% (v/v) benzyl benzoate.

Formulation G (Control) was prepared as described above in Example 2.

The PK profiles of Formulation A, Formulation H and Formulation G were evaluated in rabbits.

Figure 2:
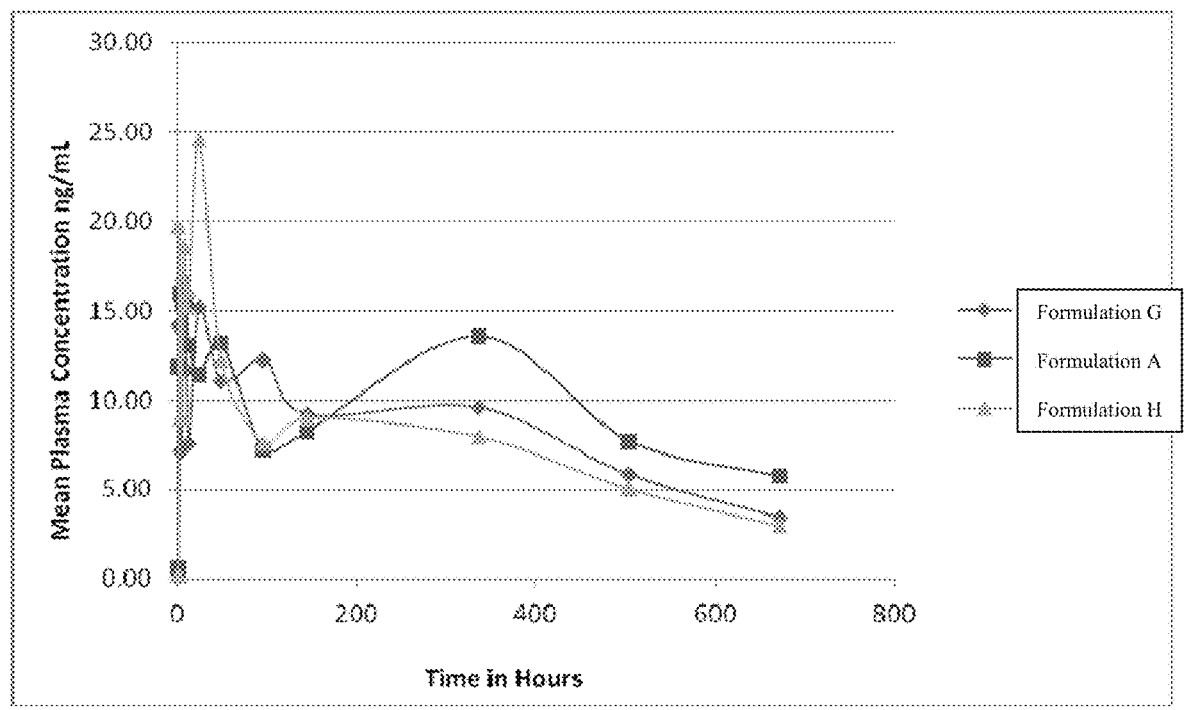
FIG. 2 is data corresponding to Example 3.

As shown in FIG. 2, inventive Formulation A and inventive Formulation H exhibited PK profiles comparable to the PK profile of Formulation G. Accordingly, as shown in Table 1 and FIG. 2, inventive Formulations A and H, are long term storage stable for at least 36 months under ambient conditions, and achieve a comparable PK profile to Formulation G, without the inclusion of castor oil.

Example 4

Fulvestrant-containing compositions (Formulation A, Formulation H and Formulation G) were prepared as follows:

Formulation A (Inventive) was prepared as described above in Example 1.

Formulation H (Inventive) was prepared as described above in Example 3.

Three separate Formulations $G_1$, $G_2$, and $G_3$ (Controls) were prepared in the same manner as Formulation G described above in Example 2.

The PK profiles of Formulation A, Formulation H, and Formulations $G_1$, $G_2$, and $G_3$ were evaluated in rabbits. The formulations were administered in an amount of 17 mg/kg rabbit body weight. Samples were drawn 28 days after administration. The PK data are presented in Table 2 below.

TABLE 2

| Formulation | $C_{max}$ (ng/mL) | $AUC_{(0-dose)}$ (mg*h/L) | $T^{1/2}$ (days) |
| --- | --- | --- | --- |
| $G_1$ | 24.4 ± 7.2 | 6.8 ± 1.2 | 9 ± 3 |
| $G_2$ | 26.3 ± 10.8 | 5.3 ± 1.6 | 12 ± 8 |
| $G_3$ | 28.7 ± 8.1 | 5.8 ± 2.9 | 20 ± 7 |
| A | 25.3 ± 11 | 6.3 ± 3.3 | 12 ± 7 |
| H | 27.6 ± 7.4 | 4.8 ± 1.2 | 38 ± 60 |

As shown in the table above, both inventive Formulations A and H exhibited similar PK profiles compared to Formulations $G_1$, $G_2$, and $G_3$.

Example 5

Additional PK studies were performed in rabbits to observe the formulations at steady state concentrations. Fulvestrant-containing compositions were prepared as follows:

Formulation G (Control) was prepared in the same manner as described above in Example 2.

Formulation A (Inventive) was prepared as described above in Example 1.

Formulation H (Inventive) was prepared as described above in Example 3.

Formulation B (Inventive) was prepared as described above in Example 1.

Formulation D (Inventive) was prepared as described above in Example 1.

The PK profiles of Formulation A, Formulation H, Formulation B, Formulation D and Formulation G were evaluated in rabbits. Doses were administered in an amount of 17 mg/kg rabbit body weight. The first dose was administered on day one, the second dose was administered on day 15, the third dose was administered on day 28, and subsequent doses (i.e. fourth, fifth, and sixth) were administered every month thereafter. Samples were drawn before each dose was administered. The PK data for the first dose, and doses four and five are reported in Table 3 below.

TABLE 3

| Dose | | Formulation G | Formulation H | Formulation D | Formulation A | Formulation B |
| --- | --- | --- | --- | --- | --- | --- |
| Dose 1 | Cmax (ng/mL) | 13.5 ± 3.1 | 7.65 ± 4.61 | 5.37 ± 3.09 | 6.66 ± 2.28 | 3.37 ± 1.11 |
| | AUC (h*ng/mL) | 887 ± 227 | 582 ± 292 | 372 ± 137 | 518 ± 188 | 254 ± 81 |
| Dose 4 | Cmax (ng/mL) | 49.3 ± 15 | 33.2 ± 4.9 | 25.3 ± 4.8 | 30.6 ± 12.0 | 18.9 ± 4.2 |
| | AUC (h*ng/mL) | 6146 ± 812 | 4897 ± 1030 | 3719 ± 780 | 4638 ± 1520 | 3260 ± 710 |
| Dose 5 | Cmax (ng/mL) | 42.4 ± 9.9 | 40.6 ± 16.4 | 48.1 ± 25.3 | 37.1 ± 14.5 | 30.3 ± 4.2 |
| | AUC (h*ng/mL) | 6243 ± 982 | 6080 ± 1290 | 4985 ± 1260 | 5668 ± 2250 | 4065 ± 775 |

As shown in Table 3 above, inventive Formulations H, D, A and B achieved steady state concentrations comparable to Formulation G after four to five doses. Table 3 shows that comparable steady state concentrations to Formulation G can be obtained without including castor oil in the formulation. Accordingly, the inventive long term storage stable compositions made in accordance with the claimed invention achieved steady state concentrations comparable to Formulation G.

Example 6

Fulvestrant-containing compositions are prepared as follows:

Formulation I (Inventive) is prepared in the same manner as Formulation A in Example 1 above, except that the MIGLYOL 812 is replaced with MIGLYOL 810, i.e. a mixture of caprylic and capric triglycerides. The volume ratio is maintained at 1:1:1:1.

Formulation J (Inventive) is prepared in the same manner as Formulation H in Example 3 above, except that MIGLYOL 812 is replaced with MIGLYOL 810, i.e. a mixture of caprylic and capric triglycerides. The volume ratio is maintained at 33:25:42.

Formulations I and J have a shelf life of at least about 24 months at 5° C. or 25° C., and are expected to be stable for at least 36 months under ambient storage conditions.

Example 7

Fulvestrant-containing compositions are prepared as follows:

Formulation K (Inventive) is prepared in the same manner as Formulation A in Example 1 above, except that the MIGLYOL 812 is replaced with MIGLYOL 818, i.e. a mixture of caprylic, capric and linoleic triglycerides. The volume ratio is maintained at 1:1:1:1.

Formulation L (Inventive) is prepared in the same manner as Formulation H in Example 3 above, except that MIGLYOL 812 is replaced with MIGLYOL 818, i.e. a mixture of caprylic, capric and linoleic triglycerides. The volume ratio is maintained at 33:25:42.

Formulations K and L have a shelf life of at least about 24 months at 5° C. or 25° C., and are expected to be stable for at least 36 months under ambient storage conditions.

Example 8

Fulvestrant-containing compositions are prepared as follows:

Formulation M (Inventive) is prepared in the same manner as Formulation A in Example 1 above, except that the MIGLYOL 812 is replaced with MIGLYOL 829, i.e. a mixture of caprylic, capric and succinic triglycerides. The volume ratio is maintained at 1:1:1:1.

Formulation N (Inventive) is prepared in the same manner as Formulation H in Example 3 above, except that MIGLYOL 812 is replaced with MIGLYOL 829, i.e. a mixture of caprylic, capric and succinic triglycerides. The volume ratio is maintained at 33:25:42.

Formulations M and N have a shelf life of at least about 24 months at 5° C. or 25° C.

Example 9

Fulvestrant-containing compositions are prepared as follows:

Formulation O (Inventive) is prepared in the same manner as Formulation A in Example 1 above, except that the MIGLYOL 812 is replaced with MIGLYOL 840, i.e. a mixture of propylene glycol dicaprylate and propylene glycol dicaprate. The volume ratio is maintained at 1:1:1:1.

Formulation P (Inventive) is prepared in the same manner as Formulation H in Example 3 above, except that MIGLYOL 812 is replaced with MIGLYOL 840, i.e. a mixture of propylene glycol dicaprylate and propylene glycol dicaprate. The volume ratio is maintained at 33:25:42.

Formulations O and P have a shelf life of at least about 24 months at 5° C. or 25° C.

We claim:

1. A fulvestrant-containing composition comprising:
   a) fulvestrant from about 50 mg/ml to about 150 mg/ml;
   b) a solvent selected from the group consisting of dimethyl sulfoxide (DMSO), glycofurol, and mixtures thereof;
   c) an oil mixture of caprylic and capric triglycerides, said oil mixture containing about 50% to about 64% $C_8$ fatty acids and about 30% to about 45% $C_{10}$ fatty acids; and
   d) benzyl benzoate as a sustained release member;
   wherein said fulvestrant-containing composition is in the form of a solution having a long-term stability defined by less than about 5% total impurities after at least about 6 months of storage at a temperature of about 40° C.;
   wherein said composition is substantially free of castor oil and castor oil derivatives; and
   wherein the volume ratio of solvent:oil mixture:sustained release member is either (i) about 33%:about 25%:about 42%, or (ii) about 2:about 1:about 1 when the solvent is a two-solvent mixture.

2. The composition of claim 1, wherein the solvent is DMSO.

3. The composition of claim 1, wherein the solvent is a mixture of DMSO and glycofurol in a volume ratio of about 1:about 1.

4. The composition of claim 1, wherein the fulvestrant concentration is from about 100 mg/ml to about 125 mg/ml.

5. The composition of claim 1, wherein the fulvestrant concentration is about 50 mg/ml.

6. The composition of claim 4, wherein the fulvestrant concentration is about 100 mg/ml.

7. The composition of claim 1, having less than about 5% total impurities, on a normalized peak area response ("PAR") basis as determined by high performance liquid chromatography ("HPLC") at a wavelength of 223 nm, after at least about 36 months of storage at a temperature of from about 5° C. to about 25° C.

8. The composition of claim 1, further comprising at least one antioxidant selected from the group consisting of lipoic acid, dihydrolipoic acid, methionine, sulpha-containing amino acids, acetone sodium bisulfate, propyl gallate, butylated hydroxytoluene ("BHT"), butylated hydroxyanisole ("BHA") and sodium formaldehyde sulfoxylate.

9. A fulvestrant-containing composition comprising:
   a) fulvestran from about 50 mg/ml to about 150 mg/ml;
   b) DMSO;
   c) a mixture of caprylic and capric triglycerides, said oil mixture containing about 50% to about 64% $C_8$ fatty acids and about 30% to about 45% $C_{10}$ fatty acids; and
   d) benzyl benzoate;
   wherein the DMSO is present in an amount of about 33% (v/v), the mixture of caprylic and capric triglycerides is present in an amount of about 25% (v/v), and the benzyl benzoate is present in an amount of about 42% (v/v);
   said fulvestrant-containing composition being in the form of a solution having a long-term stability defined by less than about 5% total impurities after at least about 6 months of storage at a temperature of about 40° C.

10. The composition of claim 9, having less than about 5% total impurities, on a normalized peak area response ("PAR") basis as determined by high performance liquid chromatography ("HPLC") at a wavelength of 223 nm, after at least about 36 months of storage at a temperature of from about 5° C. to about 25° C.

11. A fulvestrant-containing composition comprising:
a) fulvestrant from about 50 mg/ml to about 150 mg/ml;
b) DMSO;
c) a mixture of caprylic and capric triglycerides, said oil mixture containing about 50% to about 64% $C_8$ fatty acids and about 30% to about 45% $C_{10}$ fatty acids;
d) benzyl benzoate; and
e) glycofurol;
wherein the volume ratio of DMSO:mixture of caprylic and capric triglycerides:benzyl benzoate:glycofurol is about 1:about 1:about 1:about 1;
said fulvestrant-containing composition is in the form of a solution having a long-term stability defined by less than about 5% total impurities after at least about 6 months of storage at a temperature of about 40° C.

12. The composition of claim 11, having less than about 5% total impurities, on a normalized peak area response ("PAR") basis as determined by high performance liquid chromatography ("HPLC") at a wavelength of 223 nm, after at least about 36 months of storage at a temperature of from about 5° C. to about 25° C.

13. A liquid fulvestrant-containing composition consisting essentially of:
a) fulvestrant from about 50 mg/ml to about 150 mg/ml;
b) a solvent selected from the group consisting of dimethyl sulfoxide (DMSO), glycofurol, and mixtures thereof;
c) an oil mixture of caprylic and capric triglycerides, said oil mixture containing about 50% to about 64% $C_8$ fatty acids and about 30% to about 45% $C_{10}$ fatty acids; and
d) benzyl benzoate as a sustained release member;
wherein said fulvestrant-containing composition is in the form of a solution having a long-term stability defined by less than about 5% total impurities after at least about 6 months of storage at a temperature of about 40° C.;
wherein said composition is substantially free of castor oil and castor oil derivatives; and
wherein the volume ratio of solvent:oil mixture:sustained release member is either (i) about 33%:about 25%:about 42%, or (ii) about 2:about 1:about 1 when the solvent is a solvent mixture.

14. The composition of claim 1, wherein the composition does not require refrigeration to maintain long-term stability.

15. The composition of claim 9, wherein the composition does not require refrigeration to maintain long-term stability.

16. The composition of claim 11, wherein the composition does not require refrigeration to maintain long-term stability.

17. The composition of claim 13, wherein the composition does not require refrigeration to maintain long-term stability.

* * * * *